United States Patent [19]

Fein et al.

[11] 4,073,766

[45] Feb. 14, 1978

[54] ORGANIC BORATE COUPLING AGENTS

[75] Inventors: Marvin Michael Fein, Westfield; Birendra Kumar Patnaik, Parsippany; Frank K. Y. Chu, Ramsey, all of N.J.

[73] Assignee: Dart Industries, Inc., Los Angeles, Calif.

[21] Appl. No.: 750,753

[22] Filed: Dec. 15, 1976

[51] Int. Cl.$^2$ .............................................. C08K 9/04
[52] U.S. Cl. ........................... 260/42.14; 106/308 Q; 106/309; 260/37 EP; 260/37 N; 260/37 PC; 260/38; 260/39 R; 260/462 R; 428/375; 428/403
[58] Field of Search ............ 260/42.14, 462 R, 37 EP, 260/38, 39 R, 37 N, 37 PC; 106/308 Q, 309; 428/375, 403

[56] References Cited

U.S. PATENT DOCUMENTS

| | | | |
|---|---|---|---|
| 3,644,217 | 2/1972 | Cyba | 260/462 R |
| 3,697,475 | 10/1972 | Morris et al. | 260/42.14 |
| 3,766,131 | 10/1973 | Arkles | 260/42.14 |
| 3,905,936 | 9/1975 | Hawthorne | 260/42.14 |

*Primary Examiner*—James H. Derrington
*Attorney, Agent, or Firm*—Margareta LeMaire; Bryant W. Brennan; Fred S. Valles

[57] ABSTRACT

Novel coupling agents for use in filled polymers to improve physical properties e.g. melt flow and impact strength, which agents are organic borates containing at least one functional group reactive with the filler and at least one functional group compatible with the polymer.

18 Claims, No Drawings

ORGANIC BORATE COUPLING AGENTS

BACKGROUND OF THE INVENTION

The present invention relates to novel coupling compounds for use as additives in various filled or reinforced polymer resin compositions.

Fillers are generally used in polymer resin compositions as low cost extenders or pigments. They also serve to impart stiffness to molded polymer products. However, the benefits derived from incorporation of fillers are usually offset by corresponding detrimental decreaseas in many properties such as impact strength and melt flow rates. A coupling agent i.e. a compound that can form a mechanical and/or chemical bond between the filler and the resin, is therefore included in the polymer-filler composition to improve these properties. Coupling agents are also used to improve the bond between reinforcing fibers and a resin. In the past nearly all such coupling agents have been organosilanes. Other recently developed coupling agents are those containing titanium including various titanates and titanocenes, as well as other metallocenes e.g. zirconocenes and hafnocenes.

In this application the term "filler" is defined to include conventional fillers as well as reinforcing fibers.

THE INVENTION

The present invention relates to novel coupling agents, which are organic borates having the following general chemical formula:

(1)

The functional group $R_1O-$ is reactive with the hydroxyl groups of the inorganic filler to form the corresponding alcohol $R_1.OH$. $R_1$ is a linear or branched alkyl group having from 1 to 6 carbon atoms, preferably no more than 4 carbon atoms. In order to provide proper reactivity with the hydroxyl groups and to provide improved hydrolytic stability, it is preferred that $R_1$ is a secondary alkyl group.

The functional group $R_2-$ is a relatively long chained hydrocarbon group which is required to be compatible with the resin with which it is to be blended. $R_2$ therefore can have a variety of chemical structures depending upon the particular blending resin chosen, e.g. $R_2$ can be an alkyl, an aryl, or an alkaryl group. Furthermore, it can also contain various functional subgroups to impart certain additional desired properties.

For incorporation into filled or reinforced thermoplastic molding compositions, such as those based on polyolefin polymer resins, $R_2$ is suitably a linear or branched alkyl group, containing from 8 to 22 carbon atoms, preferably containing between 12 and 18 carbon atoms.

The radical X can be the same as $R_1$ or $R_2$, or be different from both $R_1$ and $R_2$, then containing special functional group or groups to impart certain desired characteristics or properties to the filled or reinforced polymer composition.

One specific aspect of this invention deals with coupling agents which are relatively simple compounds and which perform extremely well in a polymer compositions. In these coupling agents, $R_1$ is as defined above, and $R_2$ and X are independently from each other a linear or branched alkyl group containing from 8 to 22 carbon atoms, preferably between 12 to 18 carbon atoms. Such compounds are easily prepared by reacting boric acid with an alcohol $R_1OH$, wherein $R_1$ is as defined above, to produce the corresponding trialkyl borate in well known manner:

$$B(OH)_3 + 3R_1OH \rightarrow B(OR_1)_3 + 3H_2O \quad (2)$$

The trialkyl borate is then subjected to a transesterification reaction by adding thereto stoichiometric amounts of one or more alcohols i.e. either:

$$B(OR_1)_3 + 2R_2OH \rightarrow B(OR_1)(OR_2)_2 + 2R_1OH \quad (3)$$

or $$B(OR_1)_3 + R_2OH + XOH \rightarrow B(OR_1)(OR_2)(OX) + 2R_1OH \quad (4)$$

The reaction can be carried out in the presence or absence of a suitable catalyst, e.g. an alkyl titanate in an inert atmosphere. The reactor pressure is suitably maintained either at atmospheric or subatmospheric pressure, and elevated temperatures are employed, which are sufficiently high to remove the $R_1OH$ alcohol, a by-product formed in the transesterification reaction. No further treatment is required of the product obtained.

The borate coupling agents of this invention are used in quantities corresponding to between about 0.5 to about 5 percent by weight based on the weight of the filler and preferably between 1 and 3 percent by weight. The coupling agent can be included in the polymer-filler composition by a number of conventional techniques, including adding it to the polymer either before, after, or simultaneously with the addition of the filler. It can be added directly to the molten resin or as a solution in an appropriate solvent, e.g. lower alkanes. However, it is preferred that the filler be precoated with the coupling agent prior to addition to the polymer resin. No heat is required in the coating process, although can be applied if so desired.

The filler can be any one of the well known fibrous, particulate or pigment materials used for such purpose, e.g. glass fibers, asbestos, carbon fibers, calcium carbonate, alumina trihydrate, silicas, silicates, treated clays, talc, mica, carbon black, quartz, various metal powders and metallic oxides.

The polymer can be any synthetic resin including thermoplastic resins and thermoset resins. Representative of the thermoplastic resins useful in the present invention are the polyolefins, such as, polyethylene, polypropylene, polybutene-1, ethylene-propylene copolymers, as well as other olefin copolymers; styrene polymers and copolymers, vinyl chloride polymers, acrylic polymers, polycarbonate, ABS graft copolymers, nylons, etc. Typical of the thermosetting resins that may be used are epoxies, phenolic resins and urea-formaldehyde resins.

The borate coupling agents of this invention improve the dispersion of the filler throughout the polymer phase and advantageously affect various important physical properties of the polymer-filler compositions including impact strength, melt index, elongation, and heat deflection temperatures, often approaching or even surpassing the values of the respective base polymer properties. In addition, the borate coupling agents contribute to the flame retardancy of the filled polymer compositions. The coupling agents are hydrolytically stable compounds that can be stored for extended periods of time without being affected to any significant degree by humidity in the atmosphere.

In order to illustrate the invention the following examples are provided. All parts or percentages are on a weight basis unless otherwise indicated.

EXAMPLE 1

The preparation of dicetyl isopropylborate was carried out by charging 60.0 grams triisopropylborate, 154.8 grams cetyl alcohol and 2.1 grams tetrabutyltitanate catalyst to a three-necked reaction flask equipped with a stirrer, distillation head and a condenser. The stirred reaction mixture was heated to a temperature of 115°–120° C under an atmosphere of dry nitrogen. The reaction was monitored by measuring the amount of isopropyl alcohol liberated and removed from the reactor. After 2 hours the reaction was completed and the product was obtained in quantitative yields (178.5 grams). The purity of the product was confirmed by IR analysis. In a similar manner, distearyl isopropylborate and dilauryl isopropylborate were prepared by the respective reactions of stearyl alcohol and lauryl alcohol with triisopropylborate in a 2:1 mole ratio.

EXAMPLES 2–10

The beneficial effects of including borate coupling agents into calcium carbonate filled polymer compositions are demonstrated by a series of comparative experiments. The borate coupling agents, when used, were blended in a weight ratio of 3:100 with the calcium carbonate in a Henschel mixer for 3 minutes and then heated for 2 hours at 90° C. The polymer and treated filler were then compounded in a Banbury mixer at 185° C for 4–5 minutes. The polymer used in this series of experiments was an ethylene-propylene block copolymer having about 86 wt% of a propylene homopolymer block and 14 wt% of an ethylene-propylene random copolymer block. The average polymerized ethylene content of the block copolymer was about 6 wt%. The polymer to filler ratio was varied as indicated in Table 1.

As seen from the data of Examples 2, 3 and 5, the incorporation of untreated filler into the polymer results in a lowering of melt flow, impact strength and elongation properties as compared to the base polymer. With the use of filler treated with borate coupling agents, these properties are improved to a considerable extent while substantially retaining other physical properties at acceptable levels as shown by the data from the remaining examples.

EXAMPLES 11–13

Examples 11, 12 and 13 are duplicates of Examples 2, 8 9, respectively, except that the polymer base resin was a propylene homopolymer. The pertinent data from this set of experiments are shown in Table 2. Again, the beneficial effects of using borate coupling agents in the filled compositions are evident from a comparison of the analytical data.

TABLE 1

EFFECTS OF BORATE COUPLING AGENTS IN $CaCO_3$ FILLED ETHYLENE PROPYLENE COPOLYMER

| EXAMPLE | 2 | 3 | 4 | 5 | 6 | 7 | 8 | 9 | 10 |
|---|---|---|---|---|---|---|---|---|---|
| Polymer/$CaCO_3$ Ratio | 100/0 | 70/30 | 70/30 | 70/30 | 70/30 | 70/30 | 50/50 | 50/50 | 50/50 |
| Coupling Agent (1) | — | — | DS | DL | DC | DC | — | DC | DC |
| Coupling Agent/Filler Ratio | — | — | 0.03 | 0.03 | 0.03 | 0.01 | — | 0.03 | 0.01 |
| Melt Flow at 230° C, g/10 min | 5.1 | 2.8 | 3.7 | 3.3 | 3.9 | 3.2 | 0.1 | 3.8 | 0.5 |
| Notched Izod Impact, ft.lbs/in | 2.5 | 1.8 | 2.9 | 3.0 | 3.8 | 2.3 | 1.3 | 1.6 | 1.9 |
| Tensile Strength (fail), psi | 2430 | 2600 | 2500 | 2530 | 2470 | 2630 | 2460 | 2300 | 2350 |
| Tensile Strength (yield), psi | 3920 | 3120 | 3020 | 3070 | 3000 | 3130 | 2980 | 2650 | 2850 |
| Tensile Modulus - $10^5 \times$psi | 1.75 | 2.54 | 2.19 | 2.18 | 2.05 | 2.47 | 3.50 | 2.282 | 3.20 |
| Elongation (fail), % | 558 | 156 | 277 | 189 | 273 | 167 | 18 | 76 | 9.0 |
| Elongation (yield), % | 9.2 | 3.8 | 8.3 | 6.5 | 7.9 | 4.4 | 1.5 | 4.4 | 1.7 |
| Heat Deflection Temp., ° C | | | | | | | | | |
| 66 psi | 104.5 | — | — | — | — | 108.3 | 125 | 106.5 | — |
| 264 psi | 54.5 | — | — | — | — | 57.5 | 68.5 | 58 | — |

(1) DL = dilauryl isopropyborate
DC = dicetyl isopropylborate
DS = distearyl isopropylborate

TABLE 2

EFFECTS OF BORATE COUPLING AGENTS IN $CaCO_3$ FILLED PROPYLENE HOMOPOLYMER

| EXAMPLE | 11 | 12 | 13 |
|---|---|---|---|
| Polymer/$CaCO_3$ Ratio | 100/0 | 50/50 | 50/50 |
| Coupling Agent (1) | — | — | DC |
| Coupling Agent/Filler Ratio | — | — | 0.03 |
| Melt Flow at 230° C, g/10 min | 4.6 | 2.2 | 5.0 |
| Notched Izod Impact, ft.lbs/in | 0.7 | 0.7 | 0.9 |
| Tensile Strength (fail), psi | 2450 | 2760 | 2560 |
| Tensile Strength (yield), psi | 4860 | 3380 | 3120 |
| Tensile Modulus - $10^5 \times$psi | 2.23 | 4.22 | 3.58 |
| Elongation (fail), % | 41.3 | 21.0 | 52 |
| Elongation (yield), % | 11.3 | 2.4 | 4.8 |
| Heat Deflection Temp., ° C | | | |
| 66 psi | 106 | 121.8 | 115 |
| 264 psi | 58.8 | 71.3 | 62.3 |

(1) DC = dicetyl isopropylborate

It is obvious to those skilled in the art that many variations and modifications can be made to the coupling agents and filled polymer compositions of this invention. All such departures from the foregoing specification are considered within the scope of this invention as defined by the specification and claims.

What is claimed is:

1. A method of improving the properties of a filler for polymers, which comprises coating the filler with from about 0.5 to about 5 percent based on the weight of the filler of a coupling agent having the general formula

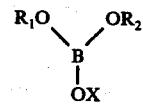

wherein $R_1$ is an alkyl group having from about 1 - 6 carbon atoms, and $R_2$ and X each is a long chained hydrocarbon group containing from 8 to 22 carbon atoms.

2. The method of claim 1 wherein $R_1$ is a branched alkyl group.

3. The method of claim 1 wherein $R_1$ is a secondary alkyl group.

4. The method of claim 1 wherein $R_2$ is an alkyl group.

5. The method of claim 4 wherein X is an alkyl group containing from 12 to 18 carbon atoms.

6. The method of claim 2 wherein $R_1$ contains from 3 to 4 carbon atoms.

7. The method of claim 6 wherein $R_1$ is isopropyl and $R_2$ and X each is an alkyl group having from 12 to 18 carbon atoms.

8. The method of claim 1 wherein the filler is precoated with from about 1 to about 3 weight percent of the coupling agent based on the weight of the filler.

9. The method of claim 1 wherein the coupling agent is dicetyl isopropylborate.

10. The method of claim 1 wherein the coupling agent is dilauryl isopropylborate.

11. The method of claim 1 wherein the coupling agent is distearyl isopropylborate.

12. The method of claim 1 wherein the filler is calcium carbonate.

13. A filler for polymers prepared by the method of claim 1.

14. A filled polymer composition containing the filler of claim 13.

15. The filled polymer composition of claim 14 wherein the polymer is a thermoplastic resin.

16. The filled polymer composition of claim 15 wherein the polymer is an olefin polymer.

17. The filled polymer composition of claim 16 wherein the polymer is an ethylene-propylene copolymer.

18. The filled polymer composition of claim 16 wherein the polymer is a propylene homopolymer.

* * * * *